United States Patent
Hindi

(10) Patent No.: US 10,888,596 B1
(45) Date of Patent: Jan. 12, 2021

(54) METHOD OF PREPARING CANNABIS EXTRACTS

(71) Applicant: Cold Baked LLC, Colorado Springs, CO (US)

(72) Inventor: Joshua Hindi, Colorado Springs, CO (US)

(73) Assignee: Cold Baked LLC, Colorado Springs, CO (US)

( * ) Notice: Subject to any disclaimer, the term of this patent is extended or adjusted under 35 U.S.C. 154(b) by 0 days.

(21) Appl. No.: 16/235,017

(22) Filed: Dec. 28, 2018

(51) Int. Cl.
*A61K 36/185* (2006.01)

(52) U.S. Cl.
CPC ........ *A61K 36/185* (2013.01); *A61K 2236/10* (2013.01); *A61K 2236/39* (2013.01)

(58) Field of Classification Search
None
See application file for complete search history.

(56) References Cited

U.S. PATENT DOCUMENTS

| | | |
|---|---|---|
| 6,730,519 B2 | 5/2004 | Elsohly et al. |
| 7,344,736 B2 | 3/2008 | Whittle et al. |
| 8,445,034 B1 | 5/2013 | Coles, Jr. |
| 8,481,091 B2 | 7/2013 | Ross |
| 8,859,016 B2 | 10/2014 | Pritchett |
| 8,895,078 B2 | 11/2014 | Mueller |
| 9,186,386 B2 | 11/2015 | Speier |
| 9,199,960 B2 | 12/2015 | Ferri |
| 9,327,210 B1 | 5/2016 | Jones |
| 9,408,417 B2 | 8/2016 | O'Connell |
| 10,238,706 B1 * | 3/2019 | Nahtigal ............... A61K 36/185 |
| 2003/0050334 A1 | 3/2003 | Murty et al. |
| 2008/0167483 A1 | 7/2008 | Whittle et al. |
| 2013/0079531 A1 | 3/2013 | Barringer |
| 2014/0248379 A1 | 9/2014 | Mueller |
| 2014/0271940 A1 | 9/2014 | Wurzer |
| 2016/0074451 A1 | 3/2016 | Speier |
| 2016/0106705 A1 | 4/2016 | Verzura et al. |
| 2016/0213720 A1 | 7/2016 | Barringer |
| 2016/0213722 A1 | 7/2016 | Jones |
| 2016/0279535 A1 | 9/2016 | Jones |
| 2016/0346339 A1 | 12/2016 | Finley et al. |
| 2017/0020944 A1 * | 1/2017 | Towle .................. A61K 36/185 |
| 2019/0083902 A1 * | 3/2019 | Nevitt .................... B01D 3/343 |
| 2019/0262304 A1 * | 8/2019 | Townsend ............ A61K 31/352 |
| 2020/0001201 A1 * | 1/2020 | Noble .................. B01D 9/0054 |
| 2020/0023286 A1 * | 1/2020 | Melnichuk ......... B01D 11/0288 |

\* cited by examiner

*Primary Examiner* — Ralph J Gitomer
(74) *Attorney, Agent, or Firm* — Brenda L. Speer, LLC; Brenda L. Speer

(57) ABSTRACT

The invention relates to a method of preparing cannabis extracts, including shatter, budder and wax extracts. The extraction method can provide a high quality and pure extraction product of THC from cannabis plant material, as either a shatter, wax or budder end extraction product. The extracted product is free of polar cannabis plant material, chlorophyll and residual solvents, has a high concentrate of THC, and can be used for dabbing, vaping or smoking consumption by a user. Suitable solvents for the method are gases selected from the group consisting of propane, butane or iso-butane, and the preferred solvent is propane. A key step of the method of the present invention is recovering solvent under atmospheric vacuum and, therefore, obtaining an extraction product that is purified of solvent and has no solvent.

10 Claims, 3 Drawing Sheets

METHOD OF PREPARING CANNABIS EXTRACTS

BACKGROUND OF THE INVENTION

Field of the Invention

The field of the invention relates to a method of preparing cannabis extracts, including shatter, budder and wax extracts.

Description of Related Art Including Information Disclosed Under 37 CFR 1.97 and 37 CFR 1.98

With the advent of medical marijuana and recreational marijuana legislation in many states of the United States of America, there is a need for quality marijuana products for consumption that can be produced in viable commercial quantity. Various methods of extracting tetrahydrocannabinol (or "THC") from cannabis plant material are known.

U.S. Pat. No. 6,730,519 issued May 4, 2004, by Elsohly et al. for Method of Preparing Delta-9-Tetrahydrocannabinol discloses a method for the isolation of delta-9-tetrahydrocannibinol (THC) from, Cannabis plant material, wherein delta-9-THC Acid and THC are separately obtained including the steps of extracting the Cannabis plant material, chelating delta-9-THC acid on alumina solid support from cannabis extracts rich in the acid washing of non-acid components of the extract with organic solvents and eluting of the delta-9-THC acid with strong polar solvents.

U.S. Pat. No. 7,344,736 issued Mar. 18, 2008, by Whittle et al. for Extraction of Pharmaceutically Active Components from Plant Materials discloses the extraction of pharmaceutically active components from plant materials, and more particularly to the preparation of a botanical drug substance (BDS) for incorporation in to a medicament. It also relates to a BDS of given purity, for use in pharmaceutical formulations. In particular, it relates to BDS comprising cannabinoids obtained by extraction from cannabis.

U.S. Pat. No. 8,455,034 issued May 21, 2013, by Coles, Jr. for Systems and Methods for Producing Organic Cannabis Tincture discloses systems and methods for fabricating a medicine by preparing a cannabis plant material and classifying the cannabis plant material into an acid, neutral, or analog form; extracting cannabinoids from the cannabis plant material by either a reflux process through evaporating and condensing the cannabis plant material or an ultrasonic extraction process of the cannabis plant material with ultrasonic waves; and infusing the cannabinoids with an alternative emulsion.

U.S. Pat. No. 8,481,091 issued Jul. 9, 2013, by Ross for Pharmaceutical Compositions discloses an improved mode of administration for cannabis and its natural and synthetic derivatives. A pharmaceutical composition suitable for sublingual aerosol or spray delivery of cannabis is provided. The formulation may be dispensed using a pump spray or the formulation may include a propellant, such as butane, 1,1,1,2-tetrafluoroethane (HFC-134a) or 1, 1, 1,2,3,3,3-heptafluoropropane (HFC-227). The term cannabis is used herein to refer to all physiologically active substances derived from the cannabis family of plants and synthetic cannabis analogues and derivatives, precursors, metabolites etc., or related substances having cannabis-like physiological effects.

U.S. Pat. No. 8,859,016 issued Oct. 14, 2014, by Pritchett for Sonically Formed Trichomic Extract Material discloses a process, product, and product by process related to sonic welding, for quickly, compressing, shaping, and decarboxylating cannabinoids; preferably from Cannabis; for oral ingestion without using any liquids or solvents; such process breaks down the Cannabis plant's cellulosic structure; increasing oil extraction; while compaction decreases transportation and storage costs, making the end product desirable as an additional ingredient in other edibles.

U.S. Pat. No. 8,895,078 issued Nov. 25, 2014, by Mueller for Method for Producing an Extract from Cannabis Plant Matter, Containing a Tetrahydrocannabinol and a Cannabidiol and Cannabis Extracts discloses a method for producing an extract from cannabis plant matter, containing tetrahydrocannabinol, cannabidiol and optionally the carboxylic acids thereof. According to said method, the dried plant matter is ground and subjected to a $CO_2$ extraction and the primary extract obtained is separated. The invention method permits $\Delta^8$ or $\Delta^9$ tetrahydrocannabinol to be selectively obtained both from industrial hemp and from drug-producing hemp, optionally after dissolving the primary extract in ethanol, separating undesirable waxes and removing the solvent under reduced pressure.

U.S. Pat. No. 9,186,386 issued Nov. 17, 2015, by Speier for Pharmaceutical Composition and Method of Manufacturing discloses methods of obtaining an extract of Cannabis plant material as well as subsequent processing of the extract to provide a concentrate of Cannabis. The present invention also provides for pharmaceutical dosage forms (e.g., oral thin films and transdermal patches) that include the concentrate (or extract) of Cannabis, as well as methods of medical treatment that include administering the pharmaceutical dosage forms.

U.S. Pat. No. 9,199,960 issued Dec. 1, 2015, by Ferri for Method and Apparatus for Processing Herbaceous Plant Materials Including the Cannabis Plant discloses a method and associated system of treating a plant material consisting essentially of the plant cannabis in order to extract cannabinoids in liquid form from the plant material. The method includes heating the plant material; drying the plant material; grinding the dried plant material into a powder form; marinating the dried plant powder in a solvent for a predetermined time period to form a marinated mixture; shaking and heating the marinated mixture; filtering the mixture so that only a liquid part of the mixture remains; and evaporating from the liquid the solvent in order to provide the cannabinoid liquid extract.

U.S. Pat. No. 9,327,210 issued May 3, 2016, by Jones for Extraction Devices, Systems, and Methods discloses extraction devices, methods, and systems are disclosed. Example devices have a solvent chamber, a plant material chamber, a collection chamber, and a solvent return that create a sealed, closed-cycle extraction and/or solvent purification process. Any extractable plant material can be used in the disclosed devices, methods, and systems although in some examples some form of the cannabis plant is used.

U.S. Pat. No. 9,408,417 issued Aug. 9, 2016, by O'Connell for Method for Preparing Tobacco Extract for Electronic Smoking Devices discloses a method and a system for preparing a tobacco extract for use in an electronic smoking device are provided. A tobacco extract and an electronic smoking device are also provided. The method includes grinding tobacco into granulated particles, and heating purified water. The method further includes injecting the heated purified water through the granulated particles of the tobacco for a predetermined period of time to produce an aqueous solution, and adding purified water to the aqueous solution. Further, the method includes heating the aqueous solution, and injecting the heated aqueous solution through ground tobacco for the predetermined period of time to produce a tobacco extract for use in the electronic smoking device.

US Patent Publication 2003/0050334 published Mar. 14, 2003, by Murty et al. for Process for extraction of Delta-9-Tetrahydrocannabinol and other Related Cannabinoids and Preparation of Specific Strength Marijuana Cigarettes discloses a process for supercritical fluid extraction of delta-9-tetrahydrocannabinol (delta-9-THC), delta-8-THC, cannabinoids or other medicinal value compounds from marijuana and other plants. Preferably, the extraction is carried out with a solvent of liquid carbon dioxide alone, or in combination with a solvent of ethanol, methanol, isopropanol, and other nonpolar/semipolar solvents at a temperature and pressure to maintain the solvents in a supercritical state. The extraction process is preferably carried out for a period of from 0 to 9 hours. The extraction process conditions result in different strengths of extracted marijuana and selective isolation of extracted compounds or mixtures of compounds. The processed marijuana leaves or other parts of the marijuana plant can be used in the manufacture of different strengths of cigarettes for the delivery of delta-9-THC or other related compounds, or as adjuvant drugs for anti-inflammatory and analgesic treatment, especially for chronic and terminal pain, neuropathic pain symptoms in humans, and in animals. Further, spiking methods can be used to make cigarettes of different strengths containing delta-9-THC or other related compounds, either synthetic or natural. Placebo cigarettes can also be prepared with pharmacologically negligible quantities of an active compound. The isolated compounds, or mixture of isolated compounds and adjuvants, of the extracted compounds can be used for the treatment of the above-mentioned symptoms, either through cigarettes or by other suitable delivery systems.

US Patent Publication 2008/0167483 published Jul. 10, 2008, by Whittle et al. for Extraction of Pharmaceutically Active Components from Plant Materials discloses the extraction of pharmaceutically active components from plant materials, and more particularly to the preparation of a botanical drug substance (BDS) for incorporation in to a medicament. It also relates to a BDS of given purity, for use in pharmaceutical formulations. In particular, it relates to BDS comprising cannabinoids obtained by extraction from cannabis.

US Patent Publication 2013/0079531 published Mar. 28, 2013, by Barringer for Process for Rapid Extraction of Active Ingredients from Herbal Materials discloses a process for the rapid extraction of active ingredients from herbal materials using a cold solvent and a very short mixing period in order to yield commercially desirable extracts. In particular, the process can be applied to the rapid extraction of cannabinoids from cannabis. The claimed invention also includes any equipment or machine, or assemblage of equipments or machines, designed or employed to utilize this process.

US Patent Publication 2014/0248379 published Sep. 4, 2014, by Mueller for Process for Producing an Extract Containing Tetrahydrocannabinol and Cannabidiol from Cannabis Plant Material, and Cannabis Extracts discloses a method for producing an extract from cannabis plant matter, containing tetrahydrocannabinol, cannabidiol and optionally the carboxylic acids thereof. According to said method, the dried plant matter is ground and subjected to a $CO_2$ extraction and the primary extract obtained is separated. The invention method permits $\Delta^8$ or $\Delta^9$ tetrahydrocannabinol to be selectively obtained both from industrial hemp and from drug-producing hemp, optionally after dissolving the primary extract in ethanol, separating undesirable waxes and removing the solvent under reduced pressure.

US Patent Publication 2014/0271940 published Sep. 18, 2014, by Wurzer for Bioactive Concentrates and Uses Thereof discloses concentrates obtained from extraction from Cannabis, preferably cannabinoid and/or terpene concentrates, and formulation of the concentrates, particularly for use for direct vaporization, infusion into edible matrices, in electronic inhalation devices, and as nutraceuticals.

US Patent Publication 2016/00774451 published Mar. 17, 2016, by Speier for Pharmaceutical Composition and Method of Manufacturing discloses methods of obtaining an extract of Cannabis plant material as well as subsequent processing of the extract to provide a concentrate of Cannabis. The present invention also provides for pharmaceutical dosage forms (e.g., oral thin films and transdermal patches) that include the concentrate (or extract) of Cannabis, as well as methods of medical treatment that include administering the pharmaceutical dosage forms.

US Patent Publication 2016/0106705 published Apr. 21, 2016, by Verzura et al. for Cannabis Extracts and Methods of Preparing and Using Same discloses the extraction of pharmaceutically active components from plant materials, and more particularly to the preparation of a botanical drug substance (BDS) for incorporation in to a medicament. It also relates to a BDS, for use in pharmaceutical formulations. In particular, it relates to BDS comprising cannabinoids obtained by extraction from cannabis.

US Patent Publication 2016/0213720 published Jul. 28, 2016, by Barringer for Process for the Extraction of Cannabinoids from Cannabis Using Lipids as an Extraction Solvent discloses processes for the extraction of cannabinoids from cannabis using lipids as an extraction solvent.

US Patent Publication 2016/0213722 published Jul. 28, 2016, by Jones for Extraction Devices, Systems, and Methods discloses extraction devices, methods, and systems. Example devices have a solvent chamber, a plant material chamber, a collection chamber, and a solvent return that create a sealed, closed-cycle extraction and/or solvent purification process. Any extractable plant material can be used in the disclosed devices, methods, and systems although in some examples some form of the cannabis plant is used.

US Patent Publication 2016/0279535 published Sep. 29, 2016, by Jones for Extraction Devices, Systems and Methods discloses extraction devices, methods, and systems. Example devices have a solvent chamber, a plant material chamber, a collection chamber, and a solvent return that create a sealed, closed-cycle extraction and/or solvent purification process. Any extractable plant material can be used in the disclosed devices, methods, and systems although in some examples some form of the cannabis plant is used.

US Patent Publication 2016/0346339 published Dec. 1, 2016, by Finely et al. for Methods for Preparation of Cannabis Oil Extracts and Compositions discloses cannabis oil extracts and compositions thereof, including cannabis oil compositions containing vitamin E, and methods for preparing the extracts and compositions. In some embodiments, the present invention provides a method for preparing a cannabis oil extract comprising eluting cannabinoids from cannabis plant material with a solvent to produce an eluate, filtering the eluate with a filter to produce a filtrate, evaporating the solvent from the filtrate with a distiller to produce a distillate, and purging the distillate under conditions sufficient to remove residual solvent, thereby preparing the extract. In some embodiments, the method further includes mixing a quantity of vitamin E with the extract to produce a cannabis oil composition.

There remains a need for an extraction method that can provide a high quality and pure extraction product of THC from cannabis plant material. Such an extraction method will provide a shatter, wax or budder end extraction product and which extraction product is free of polar cannabis plant material, chlorophyll and residual solvents, has a high concentrate of THC, and can be used for dabbing, vaping or smoking consumption by a user.

BRIEF SUMMARY OF THE INVENTION

Per the present invention, disclosed is a method of preparing a cannabis extract for a shatter product comprising the steps of: starting the method with dehydrated cannabis plant material; freezing the plant material; placing the frozen plant material in a chamber having a vessel and a gasket; integrating the chamber with a chiller column; pumping solvent gas into the chamber; filtering the solvent gas through the gasket of the chamber and the plant material in the vessel of the chamber; purifying the filtered plant material by recovering the solvent gas from the collection vessel by means of applying heat to the collection vessel, boiling off the solvent gas and pumping the collected solvent gas back into a gas holding tank; collecting the filtered plant material into a collection vessel; scraping the filtered plant material, or a cookie, out of the collection vessel; chopping the cookie into a powder; heating the powder under vacuum pressure between about 70° F. and about 110° F. from about 15 minutes to about 48 hours; heating the powder at atmospheric pressure from about 160° F. to about 210° F. until a clear and transparent shatter product is obtained; and ending the method with an obtained shatter product.

The method of the present invention to obtain a shatter product may further comprise during the step of heating the powder at atmospheric pressure, folding the powder onto itself to achieve a desired form and desired thickness for the obtained shatter product. Additionally, in the step of filtering the solvent gas through the gasket of the chamber and the plant material in the vessel of the chamber, the solvent gas is filtered through at least two filters; wherein a first filter has openings from about 10 microns to about 25 microns, and a second filter has openings from about 5 microns to about 10 microns.

Additionally, in the method of the present invention to obtain a shatter product, the chiller column is jacketed at least in part. Furthermore, the chiller column is maintained at between about −20° C. and about −40° C. to result in temperatures within the chamber being from about −5° C. to about −40° C.

Per the present invention, disclosed is a method of preparing a cannabis extract for a wax product comprising the steps of: starting the method with non-dehydrated cannabis plant material; freezing the plant material; placing the frozen plant material in a chamber having a vessel and a gasket; pumping solvent gas into the chamber; filtering the solvent gas through the gasket of the chamber and the plant material in the vessel of the chamber; purifying the filtered plant material by recovering the solvent gas from the collection vessel by means of applying heat to the collection vessel, boiling off the solvent gas and pumping the collected solvent gas back into a gas holding tank; collecting the filtered plant material into a collection vessel; scraping the filtered plant material, or a cookie, out of the collection vessel; heating the cookie with a water bath from about 125° F. to about 145° F. to boil off any residual moisture and any residual solvent gas in the cookie; stirring the cookie during the heating step until a wax product is obtained; and ending the method with an obtained wax product. Additionally, in the step of filtering the solvent gas through the gasket of the chamber and the plant material in the vessel of the chamber, the solvent gas is filtered through a filter that has openings from about 5 microns to about 50 microns.

Per the present invention, disclosed is a method of preparing a cannabis extract for a budder product comprising the steps of: starting the method with non-dehydrated cannabis plant material; freezing the plant material; placing the frozen plant material in a chamber having a vessel and a gasket; filtering the solvent gas through the gasket of the chamber and the plant material in the vessel of the chamber; purifying the filtered plant material by recovering the solvent gas from the collection vessel by means of applying heat to the collection vessel, boiling off the solvent gas and pumping the collected solvent gas back into a gas holding tank; collecting the filtered plant material into a collection vessel; scraping the filtered plant material, or a cookie, out of the collection vessel; heating the cookie with a water bath from about 130° F. to about 135° F. to boil off any residual moisture and any residual solvent gas in the cookie; stirring the cookie during the heating step until a budder product is obtained; and ending the method with an obtained budder product. Additionally, in the step of filtering the solvent gas through the gasket of the chamber and the plant material in the vessel of the chamber, the solvent gas is filtered through a filter that has openings from about 5 microns to about 50 microns.

In each of the methods of the present invention to obtain a shatter, wax or budder product, the method may further comprise a step of removing terpenes from the cookie after the step of scraping the filtered plant material, or a cookie, out of the collection vessel. Likewise, in each of the methods of the present invention, the gasket is perforated and the step of filtering the solvent gas is performed in a room having an ambient temperature of less than or equal to 75° F., and preferably less than or equal to 65° F. Further likewise, the solvent gas is selected from the group consisting of propane, butane and iso-butane, and preferably is propane.

BRIEF DESCRIPTION OF THE SEVERAL VIEWS OF THE DRAWING(S)

Figure 1:
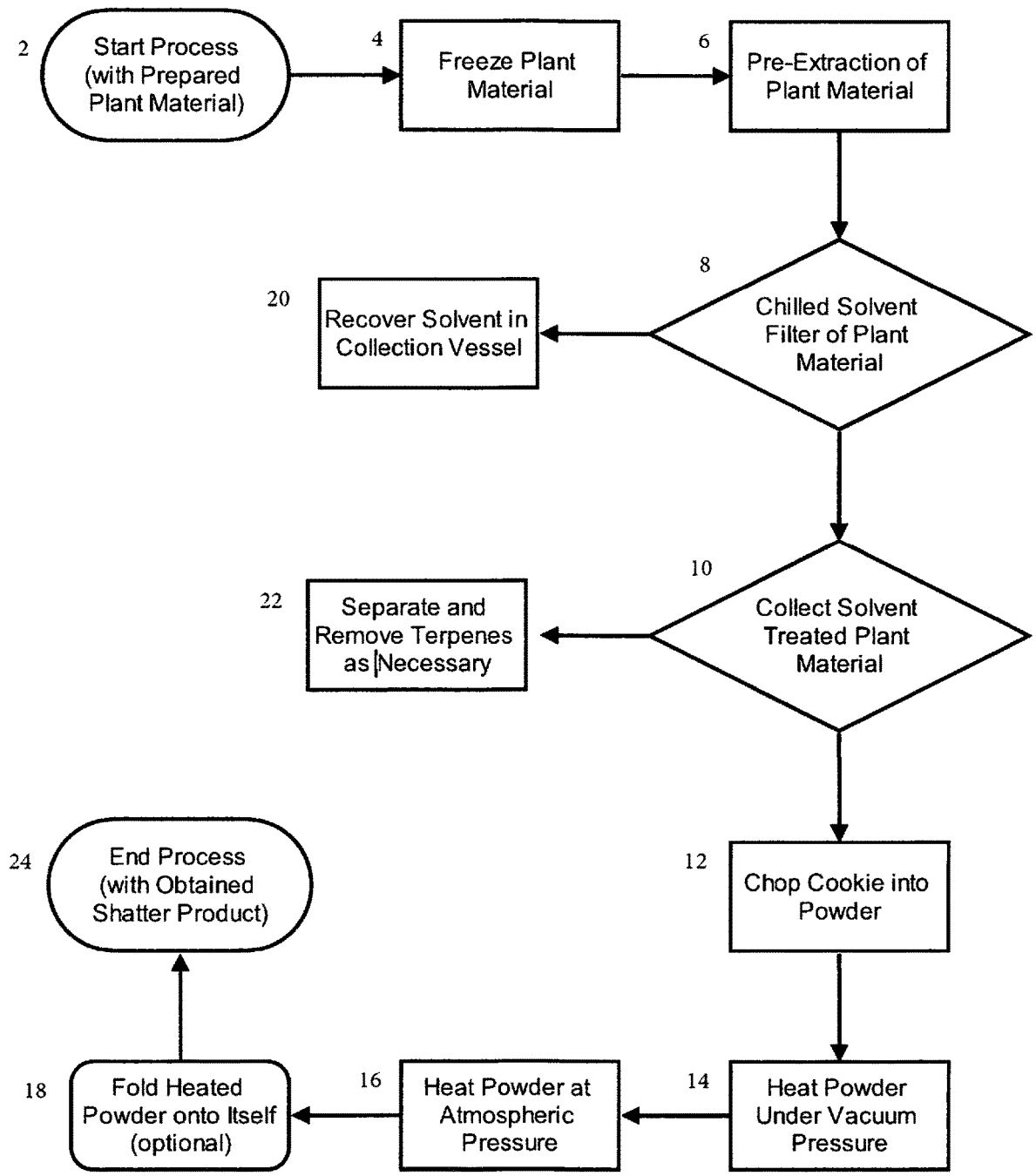
FIG. 1 is a flow diagram illustrating an embodiment of the method of the present invention for preparing a cannabis extract for a shatter product.

LIST OF REFERENCE NUMERALS 2 start process
4 freeze plant material
6 pre-extraction of plant material
8 chilled solvent filter of plant material
10 collect solvent treated plant material
12 chop cookie into powder
14 heat powder under vacuum pressure
16 heat powder at atmospheric pressure
18 fold heated powder onto itself (optional)
20 recover solvent in collection vessel
22 separate and remove terpenes as desired or necessary
24 end process with shatter product 26 unchilled solvent filter of plant material
28 heat cookie for wax product with water bath
30 end process with wax product
32 heat cookie for budder product with water bath
34 end process with budder product

DETAILED DESCRIPTION OF THE INVENTION

Three styles of consumable cannabis product are produced by the method of the present invention, namely, shatter, wax or budder (so-called and a play on words, because the cannabis bud plant material final extraction product has a consistency akin to peanut butter) products. All of these products are free of polar cannabis plant material, chlorophyll and residuals solvents, have a high concentrate of tetrahydrocannabinol (or "THC") and are used for dabbing, vaping or smoking consumption. Shatter product is a preferred product and is preferably an isolated product. The fresher the buds (or the trim or starting material), the greater the water content. As buds age, water content is lost. Fresh buds are preferred, because the greater relative water content results in less degradation of cannabinoids and terpenes in combination with the desired psychoactive plant ingredient THC which oxidizes as the buds age and dry out. Other preferred products are wax and budder products and are preferably less dehydrated or non-dehydrated products in comparison to a shatter product.

With reference to FIG. 1, in the extraction method of the present invention the starting material is buds or flowers trimmed from a cannabis plant 2. A first step in the method of the present invention is to freeze the buds or trim (plant material) in order to immobilize any water soluble in the plant material 4. The buds remain frozen and as a result any water or moisture in the material is frozen and too large to pass through filtration when dissolved in solvent. Freezing lowers the chlorophyll and other water-soluble molecules to be filtered out when solubilizing the frozen buds with solvent.

Suitable solvents are gases selected from the group consisting of propane, butane or iso-butane of 100% instrument or commercial grade. Of these suitable solvents, the least preferred solvent is iso-butane, the more preferred solvent is butane, and the most preferred solvent is propane.

With reference to FIG. 1, in performing a pre-extraction, second step 6 in the method of the present invention, frozen bud or cannabis plant material is placed in a stainless steel chamber having a vessel and a perforated gasket, such as a stainless steel pressure vessel commercially available from ETS ('The 1300' closed-loop hydrocarbon extraction system from ExtractionTek Solutions, Englewood, Colo., United States of America, www.extractiontek.com) and other manufacturers, and then a section or the entirety of the chamber is integrated within an extraction column comprising the vessel or material column, a chiller column, preferably jacketed, and a collection vessel. A perforated gasket is preferred to a solid gasket, because a perforated gasket allows the solvent to be evenly distributed over the cannabis material. The selected solvent gas is then pumped into the top of the vessel or material column that is attached to the chiller column, which solvent in turn filters through the perforated gasket and through the vessel with the cannabis material 8.

In turn, the solvent with particulate matter from the cannabis material is successfully filtered 8 through the chiller column having a minimum of two filters, a first filter having openings of about 10 to about 25 microns and a second filter having openings of about 5 to about 10 microns: wherein a second filter is placed at each end of the chiller column, and a first filter is placed on top of a second filter at an end of the chiller column connected to the vessel or material column of the chamber. Next, the filtered solute mixture is collected in the collection vessel of the extractor 20. The end result of this step is that almost all of the solvent and cannabis material mixture can be recaptured with essentially no solvent residue in the extracted cannabis material.

Figure 2:
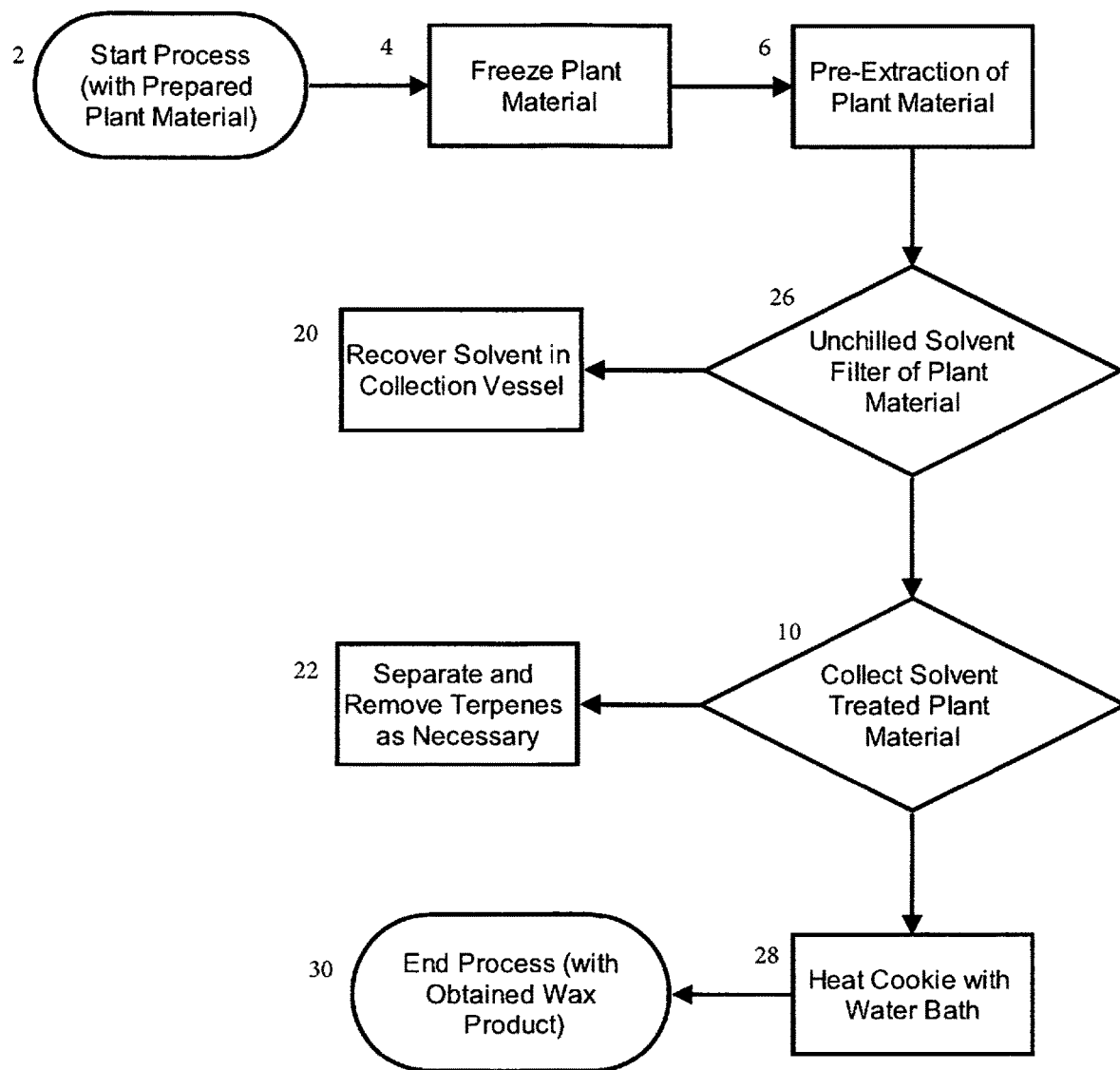
FIG. 2 is a flow diagram illustrating another embodiment of the method of the present invention for preparing a cannabis extract for a wax product.
Figure 3:
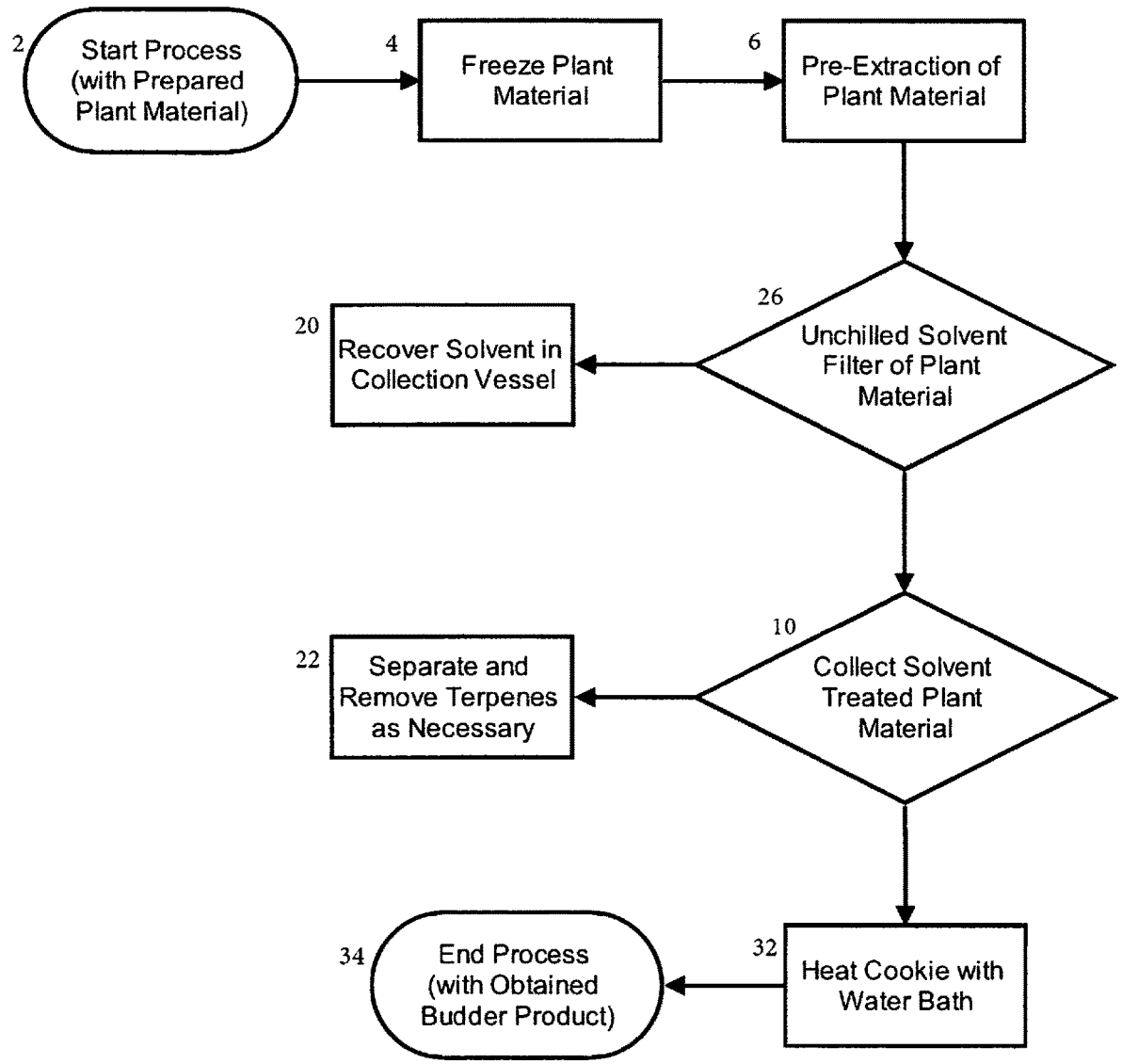
FIG. 3 is a flow diagram illustrating another embodiment of the method of the present invention for preparing a cannabis extract for a budder product.

The solvent filter step 8 is performed in a room having an ambient temperature of less than or equal to 75° F. and preferably less than or equal to 65° F. The temperature of the room is important for controlling the rate of propane evaporation. The chiller column treatment is used only for preparation of the aesthetic style of shatter end product as shown FIG. 1 and is not used for preparation of wax as an end product as shown in FIG. 2 or of budder as an end product as shown in FIG. 3.

During this pre-extraction 6, solvent filtering treatment step 8, the vacuumed cylinders are hooked up to the solvent or gas tanks. Because the gases used are instrument grade or commercial grade gases with little or no elemental oxygen, there is little to no explosion hazard. The approximate quantity of solvent to be used is based on the amount of the cannabis material and collection vessel, which solvent quantity depends on the size of the vessel and amount of cannabis material to be treated; wherein the size of the extraction chamber determines the volume of gas used. The determined appropriate solvent quantity then is run through the column. In addition, an in-line chiller column is used in order to maintain the solvent gas in a liquid state; wherein using a lower pressure maintains the solvent gas in a liquid state and the more liquid the state of the solvent, the better the solvent extracts. A valve is opened to filter the solvent into the collection vessel of the column 20.

To recover 20 the solvent from the collection vessel, heat is applied to the collection vessel via a water or chemical jacket by means of a hot water or chemical circulator. The desired solvent gas will then boil off and is pumped back into the gas holding tank. This recovery step also serves to recirculate the solvent and to achieve full recapture of the solvent gas with minimal, if any, residual solvent in the treated cannabis and extracted material. The collection vessel reaches a point of atmospheric vacuum and, therefore, the extract product is purified of solvent and has no solvent impurities. This is a key process step of the present invention and distinguishes it over the prior art.

With reference to FIG. 1, to prepare a shatter end product, a cryonic fluid is used in the chiller column to maintain the column at between −20° C. and −40° C. which results in temperatures within the chamber being from about −40° C. to about −5° C. These internal chamber temperatures serve to immobilize the lipids, fats and water-soluble molecules within the cannabis material in order to make shatter end product 24. An advantage of the method of the present invention is that this process step uses only propane to prepare shatter as an end product. In contrast, it is known in the prior art to use butane; however, full solvent recovery without any impurities in the treated material is not possible with butane. This is because the prior art process using butane results in liquid solvent butane gas having to be poured off the treated material and it is not possible to pour off all the butane, thus, solvent and chlorophyll impurities remain behind in the treated material.

Next, the solvent treated cannabis material is filtered into the collection vessel 10 and then removed from the collection vessel column after the cannabis material has been processed with the extraction steps of the method of the present invention. After treatment, the vessel is opened and the treated material can be scraped and removed from the vessel. The resultant treated material that has reached a level of atmospheric vacuum can be scraped out of the vessel and is a key process step of the present invention and distinguishes it over the prior art. With the method of the present invention, it is possible to scrape the treated material out of the vessel, because the material does not have any solvent impurities. The treated material scraped out of the vessel is a dry, dusty round disc (because the vessel is a cylinder shape) or cake of a crystalline, chalky, powdery type of material and is referred to as a 'cookie' because of its puck shape and appearance 12. This material can be either dry and powdery or a very terpene heavy liquid.

The cookie or extracted material will be sticky as a result of terpenes (liquid) in the material. At this particular stage of treatment, if the material is too liquid, it may be used to prepare a wax, budder or any other aesthetic concentrate variation as an end product, rather than a shatter end product. It is preferable to use a cookie which consists of powder or high concentrations of tetrahydrocannabinolic acid ("THCA") powder. To achieve a powder versus a liquid cookie, the terpenes in the material naturally form into balls and clump out on their own and can be separated readily from the rest of the material by scraping and physical separation 22. Depending on the preferred end product, a pure end product can be prepared from a cookie with all or a majority of the terpene components removed, or some terpenes may be retained for higher levels of flavor in the end product. The scraped terpene balls are referred to as scrape. The resulting cookie is chopped into a powder by using cutting paddles or other similar tools 12.

The broken-down cookie may be frozen once broken down. Once broken down and possibly after freezing, the cookie is then put in a vacuum oven and heated under vacuum pressure between 70° F. and 110° F. depending on terpene content 14. Once vacuumed between about 15 minutes to about 48 hours, the extracted material is removed and heated at atmospheric pressure 16, preferably by means of a stinal heat gun or similarly controlled heat source, to be slightly liquified into a treated material that has the consistency and appearance of wet sand. As the cookie is heated, optionally, it can be folded onto itself for form and desired thickness and increasingly heated into a clear and transparent "shatter" (transparent glass like) form 18. This step of additional heat application also gets rid of any residual solvent, if any, by evaporation of the solvent gas. Temperatures used in the heating process range from about 160° F., to obtain a more wet material extraction starting point, to about 210° F., to obtain a more dry material extraction starting point. The heat gun is passed over the extracted material to apply heated air to the material to rid it of any residual solvent and melts the cookie to a clear aesthetic form called shatter state. The resulting end shatter product 24 has 0 ppm (parts per million) residual solvent, contains from about 70% to about 98% THC or THCA by weight or volume, and has a color ranging from amber to bright yellow or clear, has a glass-like appearance, is mostly smooth and not sticky or tacky to the touch, and stays stable up to temperature of 70° F. The shatter can be cut up and prepared for use in doses of approximately 1 gram. Shatter products are smoked, vaporized or consumed by an end consumer.

With reference to FIG. 2, to prepare an extract that is used for a wax end product, the steps of the method of the present invention are the similar. However, in preparing wax end product, the bud material is not treated or chilled in a chiller column 26. Also, the starting cannabis material is preferably not dehydrated and has a higher moisture content. Accordingly, depending on the moisture level of the starting bud material, it can be selected to be treated and prepared as wax or shatter depending on the end product accordingly.

The cannabis material is treated in a column and processed with solvent gas to prepare an extracted material 26. The filter size used in this extraction is from about 5 microns to about 50 microns. The resulting cookie 10 will have a higher terpene content and will be more liquid or wetter and less crystalline in nature than a cookie prepared for a shatter product. This extracted cookie is placed in a vessel, such as a glass Pyrex®, pot or pan, and is heated with a water bath via a stove top burner or similar device from 125° F. to about 145° F. to boil off any moisture and any residual solvent 28. The extracted material is stirred, preferably often or continually, while it is being heated to assist in driving off the water and gas solvent. Preferably the cookie is not treated with a higher temperature range, because higher temperatures will evaporate or vaporize the terpenes resulting in a lower quality end product due to a loss in flavor. The resulting end product is a waxy substance and, thus, is referred to as a wax as an end product 30. The wax product is packaged and labeled for use by an end consumer.

With reference to FIG. 3, to prepare an extract that is used for a budder end product, the steps of the method of the present invention are the similar to those of preparing a wax end product. However, in preparing budder end product, the starting bud material is not dehydrated before extraction. Instead, the cannabis material may be decarboxylated by means of heat or selected to have a higher terpene content. The extracted material or cookie 10 is heated on a water bath from about 130° F. to about 135° F. 32. The resulting end product has a creamier texture, such as peanut butter, and, thus, is called a budder as an end product 34. The budder product is packaged and labeled for use by an end consumer.

Depending on the desired end product, whether shatter, wax or budder end product, determines which process steps of the present invention are used.

Although the present invention has been described with reference to specific embodiments, it is understood that modifications and variations of the present invention are possible without departing from the scope of the invention, which is defined by the claims set forth below. Unless defined otherwise, all technical and scientific terms used herein have the same meaning as commonly understood by one of ordinary skill in the art to which this invention belongs. Any methods and materials similar or equivalent to those described herein can also be used in the practice or testing of the present invention; however, the preferred methods and materials are now described.

The invention claimed is:

1. A method of preparing a cannabis extract for a shatter product comprising the steps of:
   freezing dehydrated cannabis plant material;
   placing the frozen plant material into a vessel of a chamber having a vessel and a gasket;
   integrating the chamber with a chiller column;
   pumping solvent gas into the chamber;
   filtering the solvent gas through the gasket and into the vessel of the chamber and through the plant material in the vessel of the chamber;
   collecting the filtered solvent gas in a collection vessel;
   purifying the filtered plant material by recovering the solvent gas from the collection vessel by means of applying heat to the collection vessel, boiling off the solvent gas and pumping recovered solvent gas back into a gas holding tank;

scraping a filtered plant material cookie from the vessel of the chamber into another collection vessel;

chopping the cookie into a powder;

heating the powder under vacuum pressure between about 70° F. and about 110° F. from about 15 minutes to about 48 hours; and heating the powder at atmospheric pressure with a heat gun that is passed over the powder to apply heated air from about 160° F. to about 210° F. to the powder until a clear and transparent shatter product results.

2. The method of claim 1, further comprising removing terpenes from the cookie after the step of scraping the cookie out of the vessel of the chamber.

3. The method of claim 1, wherein during the step of heating the powder at atmospheric pressure, also folding the powder onto itself until a desired form and desired thickness shatter product results.

4. The method of claim 1, wherein the chiller column is jacketed at least in part.

5. The method of claim 1, further wherein the gasket is perforated.

6. The method of claim 1, wherein after the step of filtering the solvent gas through the gasket and into the vessel of the chamber and through the plant material in the vessel of the chamber, then filtering the solvent gas through the chiller column having at least two filters and into the collection vessel; wherein a first filter has openings from about 10 microns to about 25 microns, and a second filter has openings from about 5 microns to about 10 microns; and wherein a second filter is placed at each end of the chiller column, and a first filter is placed on top of a second filter at an end of the chiller column integrated with the chamber.

7. The method of claim 1, wherein the step of filtering the solvent gas is performed in a room having an ambient temperature of less than or equal to 65° F.

8. The method of claim 1, wherein the chiller column is maintained at between about −20° C. and about −40° C. to result in temperatures within the chamber being from about −5° C. to about −40° C.

9. The method of claim 1, wherein the solvent gas is selected from the group consisting of propane, butane and iso-butane.

10. The method of claim 9, wherein the solvent gas is propane.

\* \* \* \* \*